United States Patent [19]

Marker et al.

[11] Patent Number: 5,504,257

[45] Date of Patent: Apr. 2, 1996

[54] PROCESS FOR PRODUCING DIISOPROPYL ETHER WITH REMOVAL OF ACID MATERIAL

[75] Inventors: Terry L. Marker, Warrenville; Robert J. Schmidt, Barrington; Richard E. Marinageli, Arlington Heights; Timothy A. Brandvold, Buffalo Grove, all of Ill.

[73] Assignee: UOP, Des Plaines, Ill.

[21] Appl. No.: 312,365

[22] Filed: Sep. 26, 1994

[51] Int. Cl.$^6$ .......................... C07C 41/01; C07C 43/04
[52] U.S. Cl. .......................... 568/694; 568/697; 568/699
[58] Field of Search .................. 568/694, 697, 568/699

[56] References Cited

U.S. PATENT DOCUMENTS

| | | | |
|---|---|---|---|
| 4,182,914 | 1/1980 | Imaizumi | 568/697 |
| 5,200,487 | 4/1993 | Lagarde et al. | 528/21 |
| 5,371,154 | 12/1994 | Brandvold et al. | 525/474 |
| 5,371,301 | 12/1994 | Marker et al. | 568/694 |
| 5,399,788 | 3/1995 | Marker | 568/697 |

OTHER PUBLICATIONS

Neier, W., Woellner, J., *Use Cation Catalyst for IPA*, Hydrocarbon Processing, Nov. 1972.

Primary Examiner—José G. Dees
Assistant Examiner—Rosalynd A. Williams
Attorney, Agent, or Firm—Thomas K. McBride; Eugene I. Snyder; Maryann Maas

[57] ABSTRACT

A process for the production of diisopropyl ether where acid is removed, without extraction, from the reactor effluent before being recycled to the reactor or being passed to downstream processing units has been developed. The process involves (1) reacting propylene and water to produce isopropyl alcohol in a reactor and reacting the isopropyl alcohol with propylene to produce diisopropyl ether in the presence of an acidic ion exchange resin catalyst to afford a reactor effluent stream containing at least water, isopropyl alcohol, diisopropyl ether, propylene, and acid, (2) passing the reactor effluent to an acid removal zone to produce an acid-depleted stream, (3) dividing the acid-depleted stream into two portions, and (4) recycling a portion to the reactor and collecting a portion.

13 Claims, 2 Drawing Sheets

PROCESS FOR PRODUCING DIISOPROPYL ETHER WITH REMOVAL OF ACID MATERIAL

BACKGROUND OF THE INVENTION

As tetraethyl lead is phased out, oxygenates have become more important in the petroleum refining industry as a source of gasoline octane boosters. The most common oxygenates for this purpose are the dialkyl ethers, especially those in the $C_s$ to $C_7$ range. One such dialkyl ether that is generating much interest is diisopropyl ether (DIPE). DIPE is in the boiling range of gasoline, has a high blending octane number, and one reactant generally used in the formation of DIPE, propylene, is a by-product commonly available in refineries. The preparation of DIPE from propylene proceeds by two sequential reactions, where propylene is first hydrated to isopropyl alcohol (IPA) (1) followed by reaction of the alcohol with the olefin (2) or by a single bimolecular dehydration reaction of the alcohol (3) (Williamson synthesis) according to the equations,

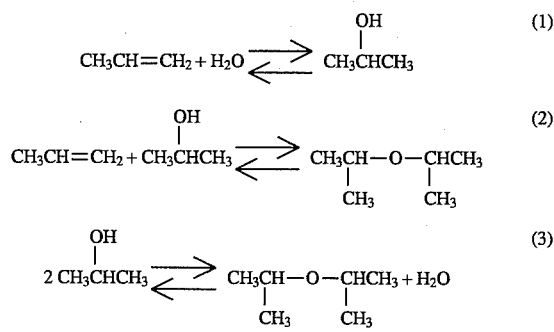

These reactions are catalyzed by a variety of catalysts such as activated charcoal, clays, resins, and zeolites. In particular, the reactions may be catalyzed by acidic ion exchange resins including sulfonated cation exchange resins such as sulfonated polystyrene resins and sulfonated styrene/divinylbenzene co-polymers as disclosed in U.S. Ser. No. 08/079,768, G.B. 1,176,620, and U.S. Pat. No. 4,182,914. Halogenated strong acid ion exchange resins such as those described in U.S. Pat. No. 4,705,808, U.S. Pat. No. 4,269,943, and U.S. Pat. No. 3,256,250 also may be used.

A recognized problem of these catalysts is their susceptibility to hydrolysis of the acidic groups causing the transfer of acidic material from the catalysts into the reaction mixture and ultimately into the reactor effluent. The hydrolysis depends strongly on the reaction temperature, and the higher the temperature the greater the degree of hydrolysis. Steps may be taken to remove acid from process streams to protect downstream process units. For example, Neier, W.; Woeliner, J., *Hydrocarbon Processing*, November 1972, discloses a process of producing IPA from 12.5:1 to 15:1 ratios of water and propylene using a fixed bed of acidic ion exchange resin where reactor effluent is neutralized with sodium hydroxide and the quenching/process water, after being separated from the product IPA, is passed through an ion exchange unit to remove sulfate, sodium, and iron ions before being recycled to the reactor.

Similarly, in U.S. Pat. No. 4,182,914 DIPE is produced from IPA and propylene in a fixed bed containing a strongly acidic ion exchange resin operated at temperatures from 100° to 130° C. The effluent of the fixed bed is passed through an inorganic, particulate acid-neutralizing agent such as magnesium oxides or aluminum oxide prior to being passed to downstream processing units. However, the portion of the effluent that is recycled to the fixed bed is not neutralized prior to recycling with no stated negative effects. Note the absence of water in this DIPE production process since IPA is added in the feedstock and not formed in the fixed bed.

When IPA is formed by olefin hydration in the same reactor where DIPE is formed by etherification of IPA and propylene, the water to olefin mole ratios may range from 0.1:1 to 2:1. Because of the quantity of water present, the reactor is operated at higher temperatures, from 130° to 150° C., thereby increasing the degree of hydrolysis of the acid groups of the acidic ion exchange resin catalyst. U.S. Ser. No. 8/079,768 discloses such a process where the IPA and DIPE are formed in a single-stage reactor and states that the amount of acid may be 10 to 100 times as high for the single-stage process in comparison to processes with very little water and lower operating temperatures. The high concentration of acid, when recycled to the reactor, substantially accelerates the deactivation of the ion exchange resin catalyst. Therefore, U.S. Ser. No. 08/079,768 discloses passing the reactor effluent to an extraction zone to transfer acid from an organic phase to an aqueous phase and then passing the aqueous phase to a base ion exchange unit to remove the acid. After the add is extracted from the organic phase, a portion of the acid-depleted organic phase is recycled to the reactor and a portion is passed to downstream processing units. Note that after extraction, the organic phase is saturated with water. Therefore, the amount of water being recycled to the reactor is not within an operator's control.

Applicants have discovered that through limiting the amount of water in the single-stage reactor to water to olefin mole ratios of from about 0.1:1 to about 0.8:1, the extraction step of U.S. Ser. No. 08/079,768 is not necessary, and the entire reactor effluent may be passed directly to an acid removal zone containing solid particles capable of retaining the acid. Eliminating the extraction step further allows an operator to control the amount of water being recycled to the reactor since the recycle is no longer saturated with water.

SUMMARY OF THE INVENTION

The purpose of the invention is to provide a process for producing diisopropyl ether where acid from the degradation of the catalyst is removed, without extraction, from the reactor effluent before being recycled to the reactor or being passed to downstream processing units. The process of the invention involves (1) reacting the propylene of a feedstock and water to produce isopropyl alcohol in a reactor and concurrently reacting the isopropyl alcohol with propylene to produce diisopropyl ether in the presence of an acidic ion exchange resin catalyst to afford a mixture containing at least water, isopropyl alcohol, diisopropyl ether, propylene, and acid; (2) passing the reactor effluent to an acid removal zone to produce an acid-depleted mixture; and (3) recycling a portion of the acid-depleted mixture to the reactor and collecting a portion of the acid-depleted mixture. A specific embodiment of the invention is one where the acid removal unit contains a base ion exchange resin or an organically-bridged polysilsesquioxane.

Still another specific embodiment of the invention is one where the propylene containing feedstock is a mixture of propane and propylene, and a portion of the acid-depleted mixture is passed to a light ends removal zone to afford a propane and propylene enriched stream, and a water, isopropyl alcohol, and diisopropyl ether enriched stream; the propane and propylene enriched stream is passed to a first separation zone to afford a propane enriched stream and a propylene enriched stream containing at least 50 mass % propylene; the propylene enriched stream is recycled to the reactor, and the propane enriched stream is collected.

Yet another specific embodiment of the invention is one where diisopropyl ether is recovered from a portion of the acid-depleted stream or from the water, isopropyl alcohol, and diisopropyl ether enriched stream by passing the stream to a second separation zone to afford a water stream, an isopropyl alcohol-water azeotrope stream, and a diisopropyl ether-isopropyl alcohol-water azeotrope stream; passing the water stream to a water wash zone, the isopropyl alcohol-water azeotrope stream to the reactor, and the diisopropyl ether-isopropyl alcohol-water azeotrope stream to a settler to afford a diisopropyl ether enriched stream and a water enriched stream; and passing the diisopropyl ether enriched stream to the water wash zone to afford an isopropyl alcohol and water stream which is passed to the second separation zone, and a diisopropyl ether product stream containing at least 96 mass % diisopropyl ether.

BRIEF DESCRIPTION OF THE DRAWINGS

FIG. I is a graphic representation of the effect on the catalyst when acid is contained in the recycle stream as compared to when acid is removed from the recycle stream.

DETAILED DESCRIPTION OF THE INVENTION

The invention applies to single stage DIPE production processes where the hydration of propylene to form IPA and the etherification of IPA and propylene to form DIPE are performed concurrently using an acidic ion exchange resin to catalyze both reactions, while protecting the reaction catalyst and downstream zones from degradation due to the introduction of acid. The invention further provides a DIPE production process which does not require breaking the IPA-water azeotrope which is formed in the process.

The process of the invention begins with introducing water and a hydrocarbon feedstock containing propylene to a reactor containing an acidic ion exchange resin catalyst. The operating conditions of the reactor include pressures of about 100 to about 1500 psia, preferably from about 700 to about 1000 psia, and temperatures of about 130° to about 180° C., preferably from about 135° to about 160° C. It is common to slowly increase the operating temperature as the catalyst ages. Suitable water to olefin mole ratios include from about 0.1:1 to about 0.8:1, preferably about 0.5:1. Greater water to olefin mole ratios may be used, but the invention would become less economically attractive, as discussed below. The propylene-containing hydrocarbon feedstock may be a refinery $C_3$ hydrocarbon stream and will most likely be a mixture of propylene and propane. The propylene-containing hydrocarbon feedstock should contain at least about 50 mass % propylene, and preferably from about 70 to about 80 mass % propylene. Suitable sources for the propylene-containing hydrocarbon feedstock include, but are not limited to, gas plant off-gas containing propylene, naphtha cracker off-gas containing light olefins, propylene from a propane dehydrogenation process, and refinery fluidized catalytic cracked (FCC) propane/propylene streams.

The acidic ion exchange resin catalysts may be any of those commonly used for a DIPE production process including sulfonated cation exchange resins such as sulfonated polystyrene resins and sulfonated styrene/divinylbenzene co-polymers. An example of a suitable sulfonated styrene/divinylbenzene co-polymer catalyst is Purolite CT-175 sold by Purolite. These sulfonated cation exchange resins are common in the art and do not require discussion here. For reference, see, U.S. Ser. No. 08/079,768, G.B. 1,176,620, and U.S. Pat No. 4,182,914. Halogenated strong acid ion exchange resins such as those described in U.S. Pat. No. 4,705,808, U.S. Pat. No. 4,269,943, and U.S. Pat. No. 3,256,250 may also be used.

As the propylene and water contact the catalyst, the hydration reaction (1) takes place and IPA is formed. As the IPA and propylene contact the catalyst, the etherification reaction (2) takes place and DIPE is formed. Reaction (3) may also take place to form DIPE, but it is less preferred due to the increased consumption of IPA as compared to reaction (2).

Figure 1:
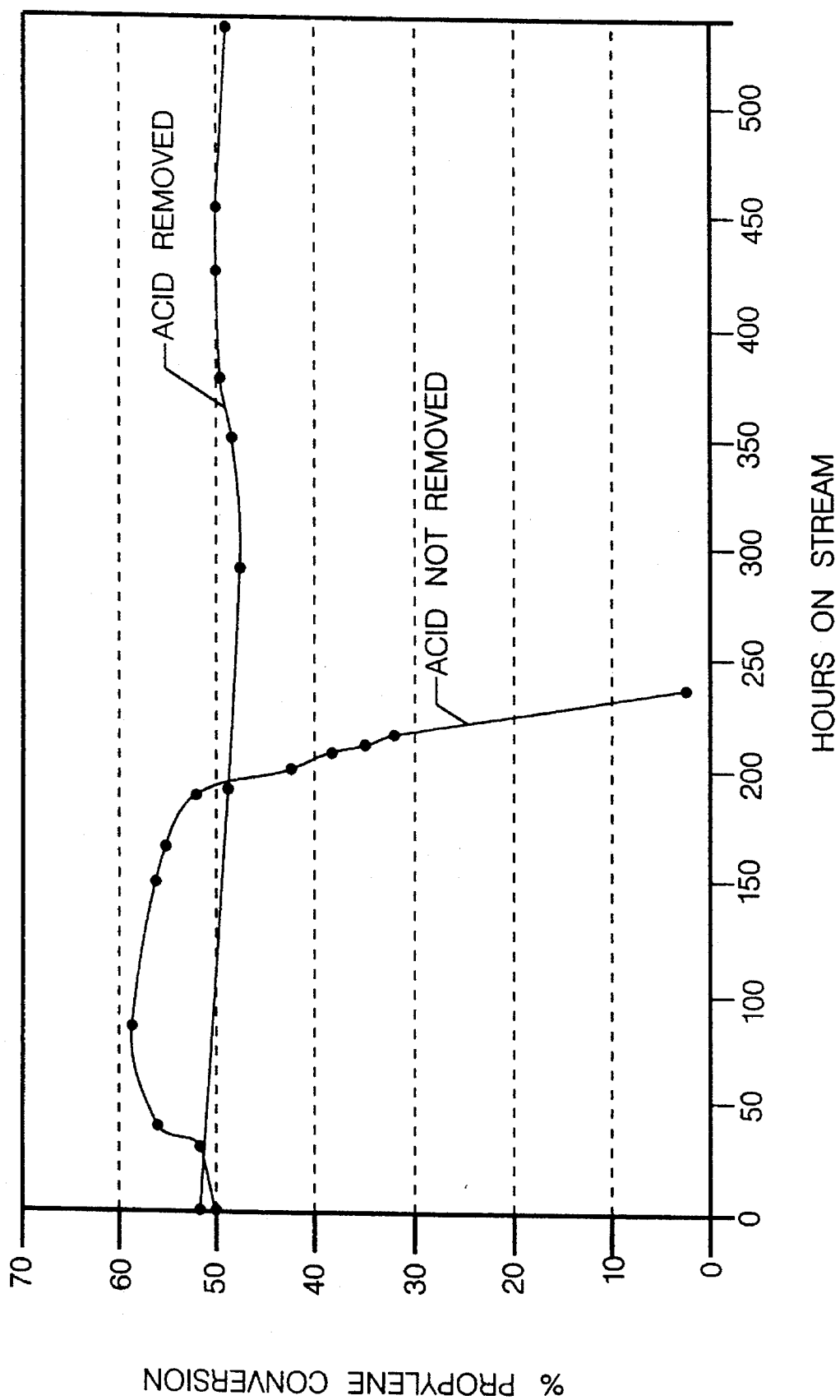

The concentration of water present in the reactor necessitates the high operating temperatures of from about 135° to about 160° C. as compared to DIPE production systems such as U.S. Pat. No. 4,182,914 operating at 100° to 130° C. The increased temperatures result in a greater degree of hydrolysis of the acid groups of the acidic ion exchange resin. Therefore, increased quantities of acid from the catalyst will enter into the reaction mixture and be carried in the reactor effluent as compared to systems containing very little water. For example, the reactor effluent may contain from as little as 1 to greater than 100 mass ppm of oxo acids of sulfur with a typical value of about 1 to about 20 mass ppm, and/or as little as 1 to greater than 100 mass ppm chloride with a typical value of about 1 to about 20 mass ppm depending upon the catalyst composition and the age of the catalyst. It is common practice to recycle a portion of the reactor effluent in order to increase conversion of propylene and IPA to DIPE and to control the temperature in the reactor. However, when the acid is not removed from the reactor effluent, and a portion of the reactor effluent is recycled to the reactor, the catalyst is rapidly deactivated as shown in FIG. 1. When the acid is removed from the reactor effluent prior to recycling, the life of the catalyst is significantly extended as shown in FIG. 1. Therefore, in the present invention, the entire reactor effluent is introduced to an acid removal zone prior to recycling. An extraction step to reduce the volume of effluent being treated in the acid removal zone is not necessary at the olefin to water mole ratios and the recycle ratios of the present invention. Olefin to water mole ratios and recycling ratios, discussed below, greater than those stated may be used, but the size of the heat exchanger equipment used with the acid removal zone would increase proportionally and may make the invention economically unattractive.

The acid removal zone contains any solid particles capable of removing the acid from the reactor effluent. For example, the solid particles may be alkaline metal oxides, base ion exchange resins, basic organically-bridged polysilsesquioxanes particles, or activated carbon, or any other strongly basic inorganic compounds with reasonable thermal stability considering the reactor effluent will be at temperatures from about 130° to about 160° C. Examples of suitable base ion exchange resins include strong base quaternary ammonium anion exchangers, amine-type weak base anion exchangers, or pyridine-type anion exchangers. Specific suitable commercial base ion exchange resins include Amberlite® IRA-67, Amberlite® IRA-68, Amberlite® IRA- 93, Amberlite®CG-420, Amberlite® IRA-410, Amberlite® IRA-900, Amberlite® IRA-904, Duolite A-7, Duolite A-368, Amberlyst A-21, Amberlyst A-26, Amberlyst A-27, Dowex 1X2-100, Dowex® 1X2-200, Dowex® 1X2-400, Dowex® 1X8-50, Dowex® 1X8-100, Dowex® 1X8-200, and Dowex® 1X8-400 which are sold by companies such as Rohm and Haas, Diamond Shamrock, or Dow. The more preferred resins are those that are stable at higher temperatures such as Amberlite® IRA-67 and Amberlite® IRA-68. These types of base ion exchange resins are readily commercially available and are very well known in the art and do not require discussion here. See generally, *Ullmann's Encyclopedia of Industrial Chemistry*, 5th ed.; Elvers, B., Hawkins, S., Ravenscroft, M., Schulz, G., Eds.; Wienham: Cambridge, New York, Vol. A14, pp. 397–398. The base ion exchange resins may be regenerated for reuse, and typically a process would contain two interchangeable base ion exchange chambers so that one chamber is in use while the base ion exchange material in the other chamber is being regenerated.

When using the base ion exchange resins, it is important to observe the thermal limitations of the resins. Most resins are stable at temperatures from ambient to a maximum of about 100° C. with a few being stable at up to 108° C. Typically the reactor effluent will be at a temperature above the maximum stable temperature of the resins. Therefore, heat exchangers are usually required to lower the temperature of the reactor effluent before entering the acid removal zone. In order to minimize the duty of the heat exchangers, the preferred base ion exchange resins are those that are stable at higher temperatures.

Suitable basic organically-bridged polysilsesquioxanes are any which are capable of removing acid from the reactor effluent. An important advantage of organically-bridged polysilsesquioxanes is that they are stable at temperatures up to about 250° to about 275° C. The reactor effluent will be at a temperature of about 130° to about 160° C. and since organically-bridged polysilsesquioxanes are stable at these temperatures, heat exchangers are not needed and the capital cost of the process is minimized. The repeating unit of the organically bridged polysilsesquioxane can best be represented two-dimensionally as:

$$\begin{bmatrix} | & | \\ -Si-X-Si-O- \\ | & | \\ O & O \\ | & | \end{bmatrix}$$

Examples of basic organically-bridged polysilsesquioxanes that are appropriate for use in the acid removal zone include those where X is a divalent radical whose parent is selected from the group consisting of dipropylamine, dipropylphenylamine, tripropylamine, and diphenylamine. Structures exemplifying such divalent radicals include:

$-CH_2-CH_2-CH_2-NH-CH_2-CH_2-CH_2-$,

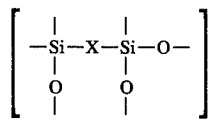

$-CH_2-CH_2-CH_2-N-CH_2-CH_2-CH_2-$,

-continued

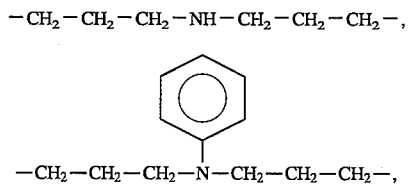

For reference, see U.S. Ser. No. 08/149,391, and Shea, K. J. Presented at the Material Research Society Spring Meeting, San Francisco, Calif. Apr. 4–8 1994.

As the reactor effluent is introduced to the acid removal zone, the acid contacts the base ion exchange resin and is exchanged with the basic group of the resin and is no longer carried with the fluid flow. Alternatively, the acid contacts the basic organically-bridged polysilsesquioxane and is removed from the fluid flow. The stream exiting the acid removal zone is acid-depleted and has an oxo acids of sulfur concentration, or an oxo acids of sulfur and chloride concentration sum of less than 0.1 mass ppm. At least a portion of the acid-depleted stream is recycled to the reactor to react the propylene and IPA to form DIPE and to control the temperature in the reactor. Suitable recycle ratios range from about 2:1 to about 10:1 and preferably 5:1. These recycle ratios are generally lower than previously used ratios of about 5:1 to 20:1 as disclosed in U.S. Ser. No. 08/079,768. The lower recycle ratios result in a reduced overall reactor effluent volume and help to make the invention of passing the entire effluent through the acid removal zone without prior extraction reasonable and economical.

At least a portion of the acid-depleted stream containing water, IPA, DIPE, propylene, and most likely, depending on the feedstock, propane, is passed to downstream processing zones to recover product DIPE. One possible downstream processing flowscheme which has the advantage of not requiring equipment to break the IPA-water azeotrope is as follows.

A portion of the acid-depleted stream is passed to a light ends fractionation zone for removal of compounds such as propylene and propane. The light ends fractionation zone may be operated at a temperature of about 80° C. and a pressure of about 235 psig. The light compounds such as propylene and propane are passed to a propylene/propane fractionation column where propane and propylene are separated into two streams. The propane enriched stream is collected, and the propylene enriched stream is recycled to the reactor. The propylene enriched stream may contain as little as 50 mass % propylene, and preferably from about 70 to about 85 mass % propylene, thereby eliminating the need for the expensive equipment required to obtain high purity propylene. The heavier compounds such as water, IPA, and DIPE are passed to a water-IPA-DIPE splitter column.

The water-IPA-DIPE splitter column is a fractionation column operating at from about 65° to about 100° C. and from about 5 to about 25 psig that separates the heavier compounds into a DIPE-IPA-water azeotrope stream, the water into another stream, and an IPA-water azeotrope into a yet another stream. The water stream is passed to a water wash zone, discussed below, and the DIPE-IPA-water azeotrope stream is passed to a settler. The IPA-water azeotrope stream is recycled to the reactor without breaking the azeotrope. This is a significant cost savings since, in order to break the azeotrope, another process unit would be required.

Furthermore, using one fractionation column to produce the three streams is more cost effective as compared to the prior art which had used two columns; see U.S. Ser. No. 08/079, 768.

In the settler, the DIPE-IPA-water azeotrope forms two phases, a DIPE enriched phase of about 95 mass % DIPE, about 1 mass % water, and about 4 mass % IPA, and a water enriched phase of about 94 mass % water, about 1 mass DIPE, and about 5 mass % IPA. The water enriched phase is recycled either directly to the water-IPA-DIPE splitter, or is combined with the IPA and water stream exiting the water wash zone; see below. The DIPE enriched phase is passed to a water wash zone.

The water wash zone is operated at from about 10° to about 66° C. and from about 1 to about 10 psig. The DIPE enriched phase and a water stream, which includes the water stream from the water-IPA-DIPE splitter, are introduced to the water wash zone in a ratio of about 1:5 to about 1:10 to form an IPA and water stream which is recycled to the water-IPA-DIPE splitter, and a DIPE stream, containing at least 96 mass % DIPE, which is collected.

Figure 2:
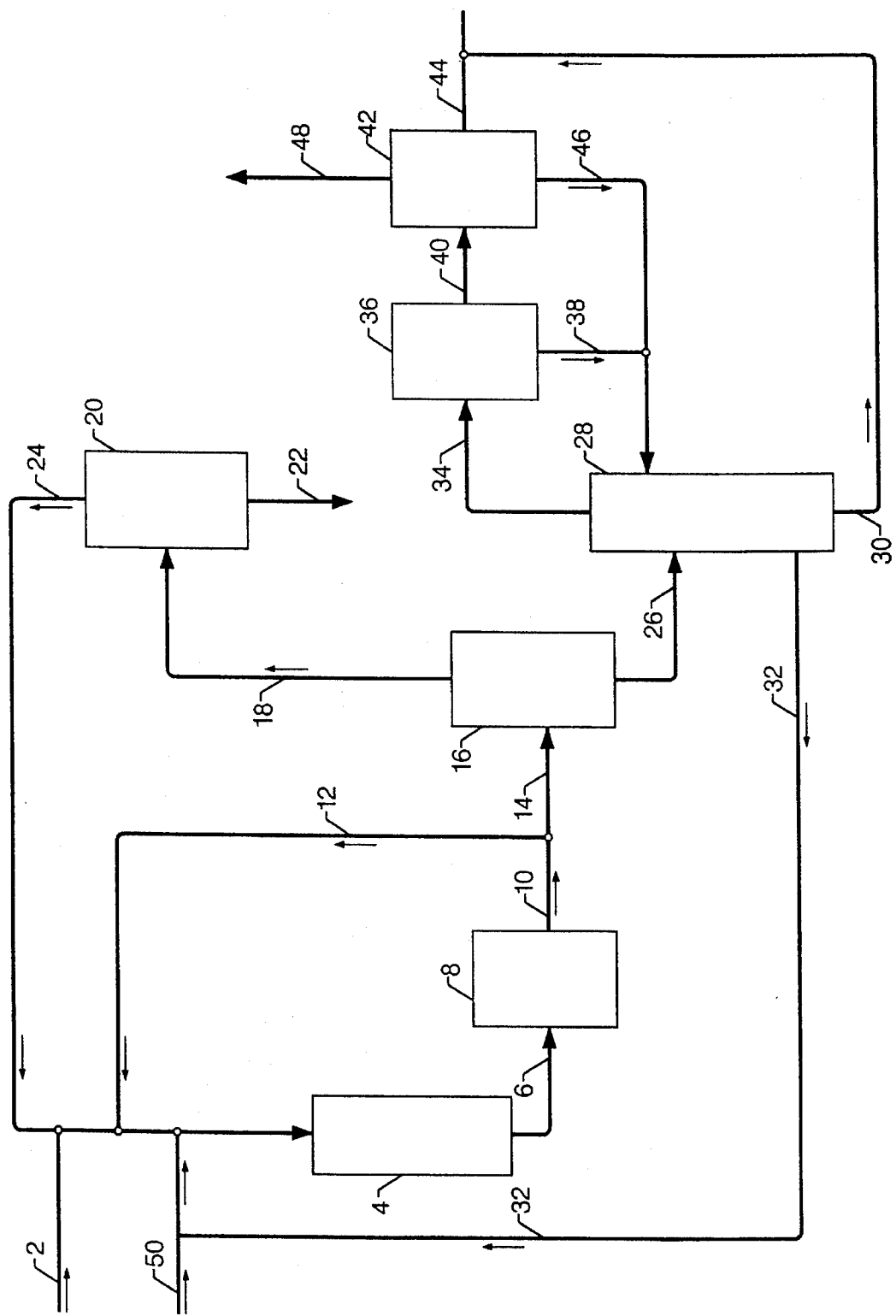
FIG. 2 is a schematic representation of the preferred embodiment of the invention.

Without intending any limitation of the scope of the present invention and as merely illustrative, the invention is explained below in specific terms as applied to a specific embodiment of the invention which is based on a design for a commercial scale unit. Referring to FIG. 2, a 70 mass % propylene-30 mass % propane feed 2 water, IPA, propylene, propane, and DIPE containing recycle 12, IPA-water azeotrope containing stream 32, and propylene-containing recycle 24 are combined and introduced to hydration and etherification reactor 4 which contains sulfonated styrene/divinylbenzene co-polymer ion exchange resin catalyst. Reactor 4 is operated at 150° C. and 1000 psig. In reactor 4, the hydrolysis of propylene is catalyzed and IPA is formed, the IPA is then catalytically reacted with propylene to form DIPE. Concurrently, the high temperature of the reactor and the presence of water cause $SO_3$ to split off from the sulfonated styrene/divinylbenzene co-polymer ion exchange resin catalyst. The $SO_3$ is then hydrolyzed to form $H_2SO_4$ which is carried into the reaction mixture. Other oxo acids of sulfur such as $HSO_3^-$ or $HSO^{4-}$ may be formed, but for ease of understanding, only $H_2SO_4$ will be discussed. The reactor effluent 6 contains propylene, propane, water, IPA, DIPE, and $H_2SO_4$, and is cooled to 80° C. via heat exchangers (not shown) before being passed to acid removal unit 8 which contains Amberlite® IRA-68 base ion exchange resin. Water feed 50 may be used to add additional water to the system if necessary. Acid removal unit 8 is operated at 80° C. and 975 psig. As the fluid reactor effluent 6 contacts the Amberlite® IRA-68 base ion exchange resin, $SO_4^=$ or $HSO^{4-}$ from the reactor effluent is exchanged for $OH^-$ or 2 $OH^-$ from the resin, which neutralizes the $H^+$ thereby resulting in an $H_2SO_4$–depleted stream 10. The $H_2SO_4$–depleted stream 10 is divided into two portions, one portion, stream 12, is recycled to reactor 4, and one portion, stream 14, is passed to a light ends recovery unit 16. The recycle to feed rate is about 5:1. Fractionation in light ends recovery unit 16 at 80° C. and 235 psig results in a propane and propylene stream 18 which is passed to a propylene-propane fractionation column 20, and a water, IPA and DIPE stream 26 which is passed to a water-IPA-DIPE splitter column 28. In the propylene-propane fractionation column 20, the propane and propylene stream 18 is separated into a propane enriched stream 22 which is collected, and a propylene enriched stream 24 which contains about 85 mass % propylene and is recycled to reactor 4. In water-IPA-DIPE splitter column 28 the water, IPA and DIPE stream 26 is fractionated to form a water stream 30, a water-IPA azeotrope stream 32, and a DIPE-IPA-water azeotrope stream 34. Water-IPA azeotrope stream 32 is recycled to reactor 4, and water stream 30 is recycled to a water wash unit 42. DIPE-IPA-water azeotrope stream 34 is passed to settler 36 where the azeotrope separates into a water rich stream 38 and a DIPE rich stream 40. DIPE rich stream 40 is passed to water wash unit 42. A water feed 44 which is combined with water stream 30 from the water-IPA-DIPE splitter column 28 is also introduced to water wash unit 42. IPA present in DIPE rich stream 40 is extracted into the water in water wash unit 42 and exits in water and IPA stream 46 which is combined with water rich stream 38 and recycled to water-IPA-DIPE splitter column 28. A DIPE product stream 48 containing at least 96 mass % DIPE is withdrawn from water wash unit 42 and collected.

What is claimed is:

1. A process for producing diisopropyl ether comprising:
   a. reacting the propylene of a feedstock containing at least 50 mass % propylene and water, where the water to propylene ratio ranges from about 0.1:1 to about 0.8:1, to produce isopropyl alcohol and concurrently reacting the isopropyl alcohol with propylene to produce diisopropyl ether in the presence of an acidic ion exchange resin catalyst to afford a mixture containing at least water, isopropyl alcohol, diisopropyl ether, propylene, and acid;
   b. treating the mixture in an acid removal zone containing solid particles capable of removing acid from the mixture to afford an acid-depleted mixture; and
   c. recycling a portion of the acid-depleted mixture to stage (a), where the recycle ratio ranges from about 2:1 to about 10:1, and collecting a second portion of the acid-depleted mixture.

2. The process of claim 1 further characterized in that the acid removal zone contains a base ion exchange resin.

3. The process of claim 2 where the base ion exchange resin is selected from the group consisting of Amberlite® IRA-67 and Amberlite® IRA-68.

4. The process of claim 1 further characterized in that the acid removal zone contains a basic organically-bridged polysilsesquioxane.

5. The process of claim 4 where the organic bridging portion of the basic organically-bridged polysilsesquioxane is selected from the group consisting of divalent radicals whose parents are selected from the group consisting of dipropylamine, dipropylphenylamine, tripropylamine, and diphenylamine.

6. The process of claim 1 where the acid-depleted mixture contains no more than about 0.1 mass ppm of oxo acids of sulfur.

7. The process of claim 1 where the acid-depleted mixture contains a sum of no more than about 0.1 mass ppm of oxo acids of sulfur and chloride.

8. The process of claim 2 where the base ion exchange resin is continuously being regenerated.

9. The process of claim 1 where the feedstock is a mixture of propane and propylene.

10. The process of claim 1 where the feedstock is a mixture of propane and propylene containing at least 70 mass % propylene.

11. The process of claim 1 where the feedstock is a mixture of propane and propylene and the process further comprises:
   a. passing the second portion to a light ends removal zone to afford a propane and propylene enriched mixture, and a water, isopropyl alcohol, and diisopropyl ether enriched mixture;

b. passing the propane and propylene enriched mixture to a first separation zone to afford a propane enriched mixture and a propylene enriched mixture containing at least 50 mass % propylene; and c. recycling the propylene enriched mixture to react with water and isopropyl alcohol, and collecting the propane enriched mixture.

12. The process of claim 11 further comprising:

a. passing the water, isopropyl alcohol, and diisopropyl ether enriched mixture to a second separation zone to afford a water mixture, an isopropyl alcohol-water azeotrope mixture, and a diisopropyl ether-isopropyl alcohol-water azeotrope mixture;

b. passing the water mixture to a water wash zone, the isopropyl alcohol-water azeotrope mixture to the reactor, and the diisopropyl ether-isopropyl alcohol-water azeotrope mixture to a settler to afford a diisopropyl ether enriched mixture, and a water enriched mixture; and c. passing the diisopropyl ether enriched mixture to the water wash zone to afford an isopropyl alcohol and water mixture which is passed to the second separation zone, and a diisopropyl ether product mixture containing at least 96 mass % diisopropyl ether.

13. The process of claim 1 further comprising:

a. passing the second portion of the acid-depleted mixture to a separation zone to afford a water enriched mixture, an isopropyl alcohol-water azeotrope mixture, and a diisopropyl ether-isopropyl alcohol-water azeotrope mixture;

b. be passing the water mixture to a water wash zone, the isopropyl alcohol-water azeotrope mixture to the reactor, and the diisopropyl ether-isopropyl alcohol-water azeotrope mixture to a settler to afford a diisopropyl ether enriched mixture, and a water enriched mixture; and c. passing the diisopropyl ether enriched mixture to the water wash zone to afford an isopropyl alcohol and water mixture which is passed to the second separation zone, and a diisopropyl ether product mixture containing at least 96 mass % diisopropyl ether.

* * * * *